(12) United States Patent
Kim

(10) Patent No.: US 9,452,140 B2
(45) Date of Patent: Sep. 27, 2016

(54) COMPOSITION OF VEGETABLE SOFT CAPSULE HAVING EXCELLENT ELASTICITY AND ADHESIVE PROPERTY, PROVIDED IN FORM OF THIN FILM, AND HAVING IMPROVED PRODUCTIVITY AND DISINTEGRATION, AND METHOD OF PREPARING THE SAME

(71) Applicant: Chang Sung Softgel System Ltd, Pocheon-si, Gyeonggi-do (KR)

(72) Inventor: Ju-su Kim, Seoul (KR)

(73) Assignee: Chang Sung Softgel System Ltd, Pocheon-si (KR)

( * ) Notice: Subject to any disclaimer, the term of this patent is extended or adjusted under 35 U.S.C. 154(b) by 0 days.

(21) Appl. No.: 14/672,857

(22) Filed: Mar. 30, 2015

(65) Prior Publication Data

US 2015/0272895 A1    Oct. 1, 2015

Related U.S. Application Data

(63) Continuation of application No. PCT/KR2014/012067, filed on Dec. 9, 2014.

(30) Foreign Application Priority Data

Apr. 1, 2014 (KR) ........................ 10-2014-0038919

(51) Int. Cl.
- *A01N 25/00* (2006.01)
- *A61K 47/34* (2006.01)
- *A61K 9/48* (2006.01)
- *A23L 1/00* (2006.01)

(52) U.S. Cl.
CPC ............ *A61K 9/4816* (2013.01); *A23L 1/0029* (2013.01); *A23V 2002/00* (2013.01)

(58) Field of Classification Search
CPC .. A61K 9/4816; A61K 47/36; A23L 1/0029; A23L 1/0522; A23V 2002/00
See application file for complete search history.

(56) References Cited

U.S. PATENT DOCUMENTS

2013/0302309 A1* 11/2013 Yang ...................... A61K 47/36
424/94.61

* cited by examiner

*Primary Examiner* — Jean Cornet
(74) *Attorney, Agent, or Firm* — Jefferson IP Law, LLP

(57) ABSTRACT

Disclosed are a composition of a vegetable soft capsule having excellent elasticity and an excellent adhesive property, provided in the form of a thin film, and having improved productivity and disintegration, and a method of preparing the same. Based on 35.3 weight part of the starch and the carrageenan, 7 weight part of the starch and 3 weight part of carrageenan are provided. In 35.3 weight part of the starch and the carrageenan, the starch contains 17.65 weight part of corn starch, 3.53 weight part of tapioca starch, and 3.53 weight part of potato starch are provided based on the weight ratio, and the carrageenan contains 7.592 weight part of iota carrageenan, 2.118 weight part of kappa carrageenan, 0.8 weight part of baking soda (sodium bicarbonate), 0.04 weigh part of arabic gum, and 0.04 weight part of Levan. Together with 35.3 weight part of the starch and the carrageenan, 17.7 weight part of glycerin, and 47 weight part of purified water are composited.

7 Claims, 1 Drawing Sheet

Process of introducing purified water and glycerin

Process of heating melting tank having purified water and glycerin

Process of rapidly introducing composition mixed at predetermined composition ratio into melting tank

Heating and stirring processes in state that composition is introduced

Heating and melting processes after stirring

Defoamation process

COMPOSITION OF VEGETABLE SOFT CAPSULE HAVING EXCELLENT ELASTICITY AND ADHESIVE PROPERTY, PROVIDED IN FORM OF THIN FILM, AND HAVING IMPROVED PRODUCTIVITY AND DISINTEGRATION, AND METHOD OF PREPARING THE SAME

CROSS-REFERENCE TO RELATED APPLICATION(S)

This application is a continuation application, claiming the benefit under §365(c), of an international application serial number PCT/KR2014/012067, filed on Dec. 9, 2014, which claimed the benefit of a Korean patent application filed on Apr. 1, 2014 in the Korean Intellectual Property Office and assigned Serial number 10-2014-0038919, the entire disclosure of which is hereby incorporated by reference.

TECHNICAL FIELD

The present invention relates to a soft capsule of a heath supplement or a medicine, and more particularly to a vegetable soft capsule having excellent elasticity and an ex adhesive property, provided in the form of a thin film, and having improved productivity and disintegration, a composition thereof, and a method of preparing the same. More specifically, the present invention relates to a vegetable soft capsule outer skin and a soft capsule including the same. In addition, the present invention relates to a vegetable soft capsule outer skin including a composition having modified starches, starch degradation products, carrageenan, a plasticizer, and a buffering agent.

BACKGROUND

Typical capsules for medicine or foods are classified into a hard capsule and a soft capsule according to the compositions of thin films of the capsules. The typical hard capsule has a material property varied depending on about 95-99 wt % of gelatin in the whole composition of the hard capsule. The soft capsule includes about 30-70 wt % of gelatin and a remainder including various types of additives used to improve a material property of the soft capsule.

In order to prepare the soft and hard thin film capsules, mammal gelatin has been used as a base to produce the thin film of the typical capsule.

However, recently, allergy according to the physical constitution of a person or aversion has been increased in relation to the use of the mammal gelatin, and the tendency to avoid the mammal gelatin has been increased by vegetarians and due to a religious background.

Accordingly, there is required the development on a soft capsule outer skin using a fish or vegetable material.

However, although various types of vegetable gelatins exist, most vegetable gelatins not only have a thick film and inferior elasticity, but also cannot be easily disintegrated.

SUMMARY

The present invention is to provide a soft capsule which can be realized with a thin film by increasing the elasticity of the film to save a source material, can improve the productivity thereof by increasing an adhesive property thereof to save cost, and can be disintegrated at a higher speed in a human body.

To this end, starch and carrageenan are used as a base and Levan is included in the carrageenan, so that the elasticity of the thin film can be improved. Accordingly, the thin film can be realized. In addition, the adhesive property can be improved, so that the source material can be saved and the productivity can be improved.

Accordingly, the soft capsule can be economically improved and includes a vegetable material so that a side effect is not made to a user of the soft capsule. In addition, the disintegration of the soft capsule can be improved to reduce the reluctance caused by a soft capsule according to the related art.

BRIEF DESCRIPTION OF THE DRAWINGS

FIG. 1 is a block diagram showing a preparation process of the present invention.

DETAILED DESCRIPTION

According to the embodiment of the present invention, there is provided a composition of a vegetable soft capsule having excellent elasticity and an ex adhesive property, provided in the form of a thin film, and having improved productivity and disintegration, the composition comprising 35.3 wt % ±10 wt % of starch and carrageenan, 17.7 wt % ±3 wt % of Glycerin, and 47 wt % ±7 wt % of purified water. The 35.3 wt % of the starch and carrageenan includes 70 wt % ±5 wt % of the starch and 30 wt % ±5 wt % of the carrageenan based on a composition ratio of the starch and carrageenan, 24.71 wt % ±1.7 wt % of the starch based on the weight ratio includes 17.65 wt % ±2 wt % of corn starch, 3.53 wt % ±1 wt % of tapioca starch, and 3.53 wt % ±1 wt % of potato starch, and 10.59 wt % ±1.7 wt % of the carrageenan based on the weight ratio includes 7.592 wt % ±1 wt % of iota carrageenan, 2.118 wt % ±0.64 wt % of kappa carrageenan, 0.8 wt % ±0.3 wt % of baking soda (sodium bicarbonate), 0.04 wt % ±0.03 wt % of arabic gum, and 0.04 wt % ±0.03 wt % of Levan.

Hereinafter, an embodiment of the present invention will be described in detail.

First, the characteristic of Levan used in the present invention will be described below.

Levan is polysaccharide fermentation produced due to microbial fermentation using sucrose as a source material. The sucrose is decomposed into glucose and fructose. The Levan is a long complex and the combination of several fructose prepared in the form of a dietary fiber.

In addition, the Levan is a low-calorie diet food which is a water-soluble dietary fiber product formed by bonding about 35 fructose molecules to about 50 fructose molecules to each other. The Levan is a functional food material which is not absorbed into a human body, but excreted from the human body. In particular, the Levan among Frutans is "resistant polysaccharides" having a superior dietary fiber function. The Levan serves as an inhibitor to inhibit cholesterol and triacylglycerol from being absorbed into intestines.

Particularly, the Levan among Frutans serving as dietary fiber accelerates the growth of bifidobacteria which are beneficial microorganisms in the intestines to perform a bowel function to prevent the growth of harmful microorganisms.

In addition, the Levan accelerates the absorption of divalent metal ions, such as $Fe^{2+}$, $Ca^{2+}$, $Mg^{2+}$, $Cu^{2+}$, and $Zn^{2+}$, into a human body.

In the following description, the mixing ratio for vegetable gelatin tin film composition cooking according to the present invention will be made.

Embodiment 1

Starch+carrageenan: 35.3 wt % ±10 wt %
Glycerin: 17.7 wt % ±3 wt %
Purified water: 47 wt % ±7 wt %

The compositions of 35.3 wt % ±10 wt % of the starch and the carrageenan are as follows in the mixing ratio for vegetable gelatin tin film composition cooking.

Embodiment 2

Starch: 70 wt % ±5 wt %
Carrageenan: 30 wt % ±5 wt %

In this case, when the starch has the content greater than that of the carrageenan beyond the error range, viscosity is increased in the formed film. When the carrageenan has the content greater than that of the starch beyond the error range, the film may not be formed.

The error ranges of the starch (24.71 wt %) and the carrageenan (10.59 wt %) among 35.3 wt % of starch and carrageenan forming the ratio of 7:3 based on the total mixing ratio of for vegetable gelatin tin film composition cooking are shown in embodiment 2.

According to the present invention, the starch (24.71 wt %) includes corn starch, tapioca starch, and potato starch, and the mixing ratio thereof is as follows.

Starch: 24.71 wt %
Corn starch: 17.65 wt % ±2 wt %
Tapioca starch: 3.53 wt % ±1 wt %
Potato starch: 3.53 wt % ±1 wt %

The corn starch is extracted an endosperm part of the corn. Among various types of starch, the corn starch has the most white and the finest powders.

In addition, if the corn starch is added to water and heated, the starch is gelatinized to generate viscosity. In this case, the viscosity is weaker than that of the potato starch. However, the viscosity of the corn starch has superior stability and a strong adhesive strength.

In addition, the corn starch gives luster. When the corn starch is heated, the corn starch provides clear and transparent light as compared with the potato starch representing strong and thick color.

The tapioca starch has a less amylose ratio so that the tapioca starch can be gelatinized. In addition, the tapioca starch may not be easily aged, so that the tapioca starch may be used for the adhesion.

The potato starch has a strong crystalline structure, a low content of protein, and a high whiteness index. In addition, if the potato starch is gelatinized, the viscosity, the water retention, and the transparency of the potato starch can be improved.

Accordingly, as the potato starch is mixed with a content corresponding to about ⅕ of that of the corn starch, the mixing ratio has the most proper reference value.

In addition, the tapioca starch is mixed with a content corresponding to about ⅕ of that of the corn starch, and mixed at the same ratio as that of the potato starch, so that the most proper viscosity can be represented.

If the corn starch and the tapioca starch have the contents beyond the error range, the tin film can be formed, and cannot have required elasticity and required thickness in the range of 0.4-0.6 mm, so that the productivity may be degraded.

For example, if the corn starch has the content exceeding the error range, the content of the potato starch or the tapioca starch must be reduced. In this case, the elasticity is degraded, so that the productivity is lowered, and the failure rate is increased to some extent, so that a production rate may be reduced.

In addition, carrageenan (10.59 wt %) mixed with the starch (24.71 wt %) at a predetermined ratio is used by mixing iota, kappa, baking soda, an Arabic gum, and Levan with each other.

The most proper mixing ratio thereof is as follows.

The mixing ratio of 10.59 wt % of carrageenan
1) Iota carrageenan: 7.592 wt % ±1 wt %
2) Kappa carrageenan: 2.118 wt % ±0.64 wt %
3) Baking soda (sodium bicarbonate): 0.8 wt % ±0.3 wt %
4) Arabic gum: 0.04 wt % ±0.03 wt %
5) Levan: 0.04 wt % ±0.03 wt %

The carrageenan according to the present invention is a material derived from *chondrus crispus*. Regarding the structure of the carrageenan, the carrageenan has a copolymer of potassium, sodium, magnesium, calcium, and ammonium sulfate ester including 3,6-anhydrous-D-galactose having the hexose of an α-1,3 or β-1,4 bond and D-galactose. The carrageenan may be classified into iota, kappa, and lambda according to the locations and numbers of sulfate having the hexose.

The iota carrageenan has the sulfate at a 2-position of the hexose, and the kappa carrageenan has one sulfate per disaccharide unit.

The iota carrageenan according to the present invention forms a normal gel, and the kappa carrageenan forms a hard gel.

Therefore, the content of the iota carrageenan has the content that is three times greater than that of the kappa carrageenan for forming the hard gel.

In this case, when the content of iota is increased, a film may not be smoothly formed. Even if the film is formed, the film may not be smoothly molded and bonded, so that the failure rate is increased, and the hardness of the carrageenan may be reduced.

In addition, when the content of the kappa is increased, more than a required hardness is obtained, so that the film may not easily formed, and the adhesion property is degraded, so that the failure rate may be increased.

In addition, sodium bicarbonate (soda) is used as an antacid agent. The sodium bicarbonate is used with the content corresponding to about ⅒ of carrageenan for the mixing.

In this case, when the content of the sodium bicarbonate is changed, pH of the vegetable thin film composition becomes in the range of 7 to 10, that is, alkalescence, so that the film hardness is maintained at a value appropriate to form and bond the thin film.

According to the present invention, when the content of the sodium bicarbonate is 0.4 wt % exceeding the upper limit value of the error range, the same effect can be made.

The Arabic gum is a kind of gum such as carrageenan. Even if a small amount of Arabic gum is added, the effect is increased, wherein exerts an influence on forming of a thin film, the adhesive property of the thin film, and the elasticity of the thin film, so that the productivity can be improved.

The upper limit of the error range may be increased.

According to the present invention, if the upper limit of the error range is increased to 0.09 wt %, the same effect can be obtained.

The Levan is used to increase the adhesive property, the elasticity according to the thin films, or rapid disintegration in the above-described capsulation process.

In this case, when the content of the Levan is changed, that is, when the content of the Levan exceeds the error range, cost may be increased due to a high-price source material and a great amount of moisture is absorbed, so that the film can be interrupted from being formed. When the content of the Levan is less than the error range, the adhesive property and the disintegration may be degraded, which exerts an influence on the productivity and the quality.

The maximum value in the content of the Levan may be used to 0.09 wt % from the error range.

In addition to the starch and the carrageenan, glycerin serving as a plasticizer is used for formability. The glycerin is used to the extent of about ⅕ of the whole weight. If possible, it is preferred that the glycerin is used to a value lower than ⅕ of the whole weight.

According to the present invention, the glycerin (plasticizer) is used in the range of 17.7 wt % ±3 wt %.

If the content of the glycerin is lower than the error range, the capsule hardness is increased, so that a gelatin ribbon is cut, and the adhesive property is degraded, so that the failure occurs. If the content of the glycerin is higher than the error range, the hardness is decreased, and the elasticity is lowered, so that the ribbon may not be easily formed, and the capsule may be torn in the state of the finished product.

Purified water is used as a solvent to mix the above materials with each other. When general purified water is used, since the general purified water contains various types of minerals, a required appearance cannot be obtained.

According to the present invention, the purified water is used by about ½ of the whole weight for mixing. If possible, the purified water is preferably used in an amount less than ½ of the whole weight.

According to the present invention, the purified water is used in the content of 47 wt % ±7 wt %.

In addition, when an amount of the purified water is greater than the error range, the gelatinization is increased, so that the gelatin film may not be completely formed. When the amount of the purified water is less than the error range, the gelatinization is decreased, so that the hardness is increased. Accordingly, the thin film may not be formed.

When the capsule is formed using the above compositions, the thickness of the formed ribbon can be obtained to the thickness of 0.4-0.6 mm. Seal Late represents the ratio of the thickness of a bonding part to a surficial thickness. Since the thickness of the bonding part can be maintained to 60-80% of the surficial thickness, the superior elasticity and the superior adhesive property can be obtained. In addition, due to the thin film, the productivity can be improved and the disintegration can be improved, so that the vegetable soft capsule can be obtained.

In addition, the capsule can be formed at 5 rpm twice faster than 2.5 rpm according to the related art at a die roll having a diameter of 150 mm and the length of 250 mm due to the increase in the adhesive property and the tension (elasticity) resulting from the bonding ratio corresponding to 60-80% of the gelatin ribbon according to the present invention.

In addition, when the gelatin ribbon is formed with the above composition, the gelatin ribbon has clear and transparent color when comparing with other product. In addition, the introduction of foreign matters can be determined with naked eyes of a user, so that the gelatin ribbon can be maintained in a clean state.

In addition, if a temperature, time, and a speed are not maintained in the gel cooking using the above compositions, the viscosity and the tension are changed, and bubbles are formed, so that the function of the gel ribbon may be degraded.

Regarding the condition of a preparation method of the soft capsule to solve the above problems, according to the present invention, the temperature of a melting tank, a heating temperature, and the temperature for defoamation allowed the error range of ±3° C., and the rotational speed in stirring was allowed the error range of ±3 rpm. When the error range is ±5 mins, the object of the present invention can be accomplished.

However, the error ranges are made by taking into consideration economical aspects. If the economical aspects are not taken into consideration, the above error range may not be the above range.

The preparation method according to the present invention, a first process of introducing the purified water and the glycerin into the melting tank is performed.

In this case, the glycerin remaining in a vessel is cleaned using a slight amount of purified water for the introduction into the melting tank.

Thereafter, a second process of setting the temperature of the melting tank to 70° C.±3° C. and heating the melting tank to an upper limit value is performed.

In this case, if an agitator is operated at the speed of 15 rpm±3, the stirring work may be more excellently performed when the compositions are introduced in a third process which is the next process.

Thereafter, according to the third process, when the temperature of the melting tank is in the range of 60° C. to 70° C., the compositions mixed at the composition ratio can be rapidly introduced into the melting tank.

In this case, the compositions must be introduced within the shortest time if possible. If the time to introduce the compositions is increased, a great amount of bubbles are generated to change the viscosity and the tension as described above. Accordingly, the function of the gel ribbon may be degraded.

In this case, if the stirring work is not smoothly performed in the state that the compositions are introduced, a user may open the cover of the melting tank and remove powder-phase compositions attached to the agitator and the paddle.

The, according to the fourth process, the heating work and the stirring work are performed. According to the present invention, the heating work is performed at a heating temperature in a range of 70° C.±3° C. for a heating time in a range of 15 to 20±5 minutes and a stirring work is performed at a rotational speed of an agitator and a paddle in a range of 15±3 rpm If the heating temperature, the heating time, or the stirring speed deviates from the error range, the viscosity and the tension may be changed, and the bubbles may be generated, so that the function of the gel ribbon may be degraded.

A fifth process of performing a heating work to a temperature in a range of 90° C.±3° C. after the stirring work is finished in the fourth process for a heating time in a range of 60±5 minutes, and performing stirring and melting works at a rotational speed of the agitator and the paddle in a range of 25±3 rpm is performed.

After the melting work has been finished through the heating work as described above, a sixth process, which is a defoamation process to remove bubbles, is performed by actuating a vacuum pump.

In this case, the temperature of the vacuum pump is maintained in the range of 80° C.±3° C.

After bubbles have been removed as described, a process for a service tank is performed.

What is claimed is:

1. A composition of a vegetable soft capsule having excellent elasticity and an excellent adhesive property, provided in a form of a thin film, and having improved productivity and disintegration, the composition comprising:
- starch and carrageenan having a content in a range of 35.3 wt % ±10 wt %;
- glycerin having a content in a range of 17.7 wt % ±3 wt %; and
- purified water having a content in a range of 47 wt % ±7 wt %,
- wherein the starch and carrageenan having the content in the range of 35.3 wt % ±10 wt % contains the starch having a content in a range of 70 wt % ±5 wt % of the starch and carrageenan and the carrageenan having a content in a range of 30 wt % ±5 wt % of the starch and carrageenan,
- wherein 24.71 wt % ±1.7 wt % of the starch contains 17.65 wt % ±2 wt % of corn starch, 3.53 wt % ±1 wt % of tapioca starch, and 3.53 wt % ±1 wt % of potato starch, and
- wherein 10.59 wt % ±1.7 wt % of the carrageenan contains 7.592 wt % ±1 wt % of iota carrageenan, 2.118 wt % ±0.64 wt % of kappa carrageenan, 0.8 wt % ±0.3 wt % of baking soda (sodium bicarbonate), 0.04 wt % ±0.03 wt % of arabic gum, and 0.04 wt % ±0.03 wt % of Levan.

2. A method of preparing a vegetable soft capsule having excellent elasticity and an excellent adhesive property, provided in a form of a thin film, and having improved productivity and disintegration, the method comprising:
- introducing purified water and glycerin into a melting tank according to the content as recited in claim 1;
- heating the melting tank having the purified water and the glycerin to 70° C.±3° C.;
- mixing starch and carrageenan according to the content as recited in claim 1 and introducing the mixture into the melting tank when the temperature of the melting tank is in a range of 60° C. to 70° C.;
- heating the melting tank at a heating temperature in a range of 70° C.±3° C. for a heating time in a range of 15 to 20±5 minutes and stirring the melting tank at a rotational speed in a range of 15±3 rpm by an agitator and a paddle
- heating the melting tank at a temperature in a range of 90° C.±3° C. for a heating time in a range of 60±5 minutes after the stirring is finished, and stirring and melting at a rotational speed in a range of 25±3 rpm by the agitator and the paddle; and
- removing any bubbles formed in the mixture using a vacuum pump maintained in a range of 80° C.±3° C. after the melting is finished.

3. The method of claim 2, wherein the composition of starch and carrageenan is introduced into the melting tank within a shortest time when the temperature of the melting tank is maintained in the range of 60° C. to 70° C. through the second process, such that a function of a gel ribbon is prevented from being degraded as a great amount of bubbles are generated due to delay of the introduction of the composition to change viscosity and tension.

4. The method of claim 2, wherein the capsule is formed at a rotational speed of 5 rpm which is twice higher than a conventional rotational speed of 2.5 rpm at a die roll having a diameter of 150 mm and a length of 250 mm due to increase in an adhesive property and tension (elasticity) resulting from a bonding ratio corresponding to a range of 60% to 80% of the gelatin ribbon according to the methods of claim 2.

5. The method of claim 2, wherein a gelatin ribbon prepared according to the method of claim 2 has excellent elasticity and an excellent adhesive property, is provided in a form of a thin film, and has improved productivity and disintegration.

6. The method of claim 3, wherein the capsule is formed at a rotational speed of 5 rpm which is twice higher than a conventional rotational speed of 2.5 rpm at a die roll having a diameter of 150 mm and a length of 250 mm due to increase in an adhesive property and tension (elasticity) resulting from a bonding ratio corresponding to a range of 60% to 80% of the gelatin ribbon according to the method of claim 2.

7. The method of claim 3, wherein the gelatin ribbon prepared according to the methods of claim 2 has excellent elasticity and an excellent adhesive property, is provided in a form of a thin film, and has improved productivity and disintegration.

* * * * *